US 7,670,368 B2

(12) United States Patent
Hill et al.

(10) Patent No.: US 7,670,368 B2
(45) Date of Patent: Mar. 2, 2010

(54) VENOUS VALVE APPARATUS, SYSTEM, AND METHOD

(75) Inventors: Jason P. Hill, Cottage Grove, MN (US); Joseph M. Thielen, Buffalo, MN (US); William J. Drasler, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 798 days.

(21) Appl. No.: 11/052,655

(22) Filed: Feb. 7, 2005

(65) Prior Publication Data

US 2006/0178730 A1 Aug. 10, 2006

(51) Int. Cl.
  *A61F 2/06* (2006.01)
  *A61F 2/24* (2006.01)
(52) U.S. Cl. .................................................. 623/1.24
(58) Field of Classification Search ......... 623/2.1–2.19, 623/1.11–1.5
See application file for complete search history.

(56) References Cited

U.S. PATENT DOCUMENTS

| | | | | |
|---|---|---|---|---|
| 3,671,979 A | 6/1972 | Moulopoulos | ...................... | 3/1 |
| 4,291,420 A | 9/1981 | Reul | .............................. | 3/1.5 |
| 4,787,901 A | 11/1988 | Baykut | ........................... | 623/2 |
| 4,872,874 A | 10/1989 | Taheri | ............................ | 623/1 |
| 4,935,030 A | 6/1990 | Alonso | ........................... | 623/2 |
| 4,994,077 A | 2/1991 | Dobben | ......................... | 623/2 |
| 5,002,567 A | 3/1991 | Bona et al. | ..................... | 623/2 |
| 5,141,491 A | 8/1992 | Bowald | ......................... | 604/22 |
| 5,163,953 A | 11/1992 | Vince | ............................. | 623/2 |
| 5,219,355 A | 6/1993 | Parodi et al. | ................. | 606/191 |
| 5,254,127 A | 10/1993 | Wholey et al. | .............. | 606/153 |
| 5,327,774 A | 7/1994 | Nguyen et al. | ................. | 73/37 |
| 5,332,402 A | 7/1994 | Teitelbaum | ..................... | 623/2 |
| 5,370,685 A | 12/1994 | Stevens | ......................... | 623/2 |
| 5,411,552 A | 5/1995 | Anderson et al. | .............. | 623/2 |
| 5,469,868 A | 11/1995 | Reger | .......................... | 128/898 |
| 5,480,423 A | 1/1996 | Ravenscroft et al. | ........... | 623/1 |
| 5,500,014 A | 3/1996 | Quijano et al. | ................. | 623/2 |
| 5,545,214 A | 8/1996 | Stevens | ......................... | 623/2 |
| 5,554,185 A | 9/1996 | Block et al. | ..................... | 623/2 |
| 5,643,208 A | 7/1997 | Parodi | .......................... | 604/96 |
| 5,693,087 A | 12/1997 | Parodi | ........................... | 623/1 |
| 5,713,953 A | 2/1998 | Vallana et al. | .................. | 623/2 |
| 5,716,370 A | 2/1998 | Williamson, IV et al. | ... | 606/153 |
| 5,735,859 A | 4/1998 | Fischell et al. | .............. | 606/108 |
| 5,741,326 A | 4/1998 | Solovay | .......................... | 623/1 |

(Continued)

FOREIGN PATENT DOCUMENTS

EP  0 380 666  8/1990

(Continued)

OTHER PUBLICATIONS

US 6,673,110, 01/2004, Alfieri et al. (withdrawn)

(Continued)

*Primary Examiner*—Corrine McDermott
*Assistant Examiner*—Cheryl Miller
(74) *Attorney, Agent, or Firm*—Brooks, Cameron & Huebsch, PLLC

(57) ABSTRACT

A venous valve with a frame and a cover on the frame for unidirectional flow of a liquid through the valve.

14 Claims, 10 Drawing Sheets

U.S. PATENT DOCUMENTS

| | | | |
|---|---|---|---|
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 6,010,531 A | 1/2000 | Donlon et al. | 623/2 |
| 6,042,607 A | 3/2000 | Williamson, IV et al. | 623/2 |
| 6,139,575 A | 10/2000 | Shu et al. | 623/2.12 |
| 6,287,334 B1 | 9/2001 | Moll et al. | 623/1.24 |
| 6,312,447 B1 | 11/2001 | Grimes | 606/219 |
| 6,355,030 B1 | 3/2002 | Aldrich et al. | 606/28 |
| 6,402,780 B2 | 6/2002 | Williamson, IV et al. | 623/2.11 |
| 6,419,696 B1 | 7/2002 | Ortiz et al. | 623/2.37 |
| 6,425,916 B1 | 7/2002 | Garrison et al. | 623/2.11 |
| 6,440,164 B1 | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 | 1/2003 | Pavcnik et al. | 623/1.15 |
| 6,564,805 B2 | 5/2003 | Garrison et al. | 128/898 |
| 6,569,196 B1 | 5/2003 | Vesely | 623/2.14 |
| 6,602,286 B1 | 8/2003 | Strecker | 623/1.24 |
| 6,629,534 B1 | 10/2003 | St. Goar et al. | 128/898 |
| 6,635,085 B1 | 10/2003 | Caffey et al. | 623/2.1 |
| 6,666,885 B2 | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |
| 6,974,464 B2 | 12/2005 | Quijano et al. | 606/108 |

| Patent/Pub No. | Date | Inventor | Class |
|---|---|---|---|
| 6,974,474 B2 | 12/2005 | Pavcnik et al. | 623/1.24 |
| 6,974,476 B2 | 12/2005 | McGuckin, Jr. et al. | 623/2.4 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | 606/139 |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lahsinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.13 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/139 |
| 7,089,051 B2 | 8/2006 | Jäverud et al. | 600/547 |
| 7,090,695 B2 | 8/2006 | Solem et al. | 623/2.37 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0099439 A1 | 7/2002 | Schwartz et al. | |
| 2002/0123802 A1 | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Liddicoat et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |

| Publication No. | Date | Inventor | Class |
|---|---|---|---|
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1* | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0249452 A1 | 12/2004 | Adams et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | Dimatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075723 A1 | 4/2005 | Schroeder et al. | 623/2.1 |
| 2005/0075724 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075728 A1 | 4/2005 | Nguyen et al. | 623/2.17 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 606/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |

| Pub. No. | Date | Inventor | Class |
|---|---|---|---|
| 2005/0137701 A1 | 6/2005 | Salahieh et al. | 623/2.38 |
| 2005/0137702 A1 | 6/2005 | Haug et al. | 623/2.38 |
| 2005/0143807 A1* | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0177601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Startksen et al. | 604/510 |
| 2006/0025784 A1 | 2/2006 | Startksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |

| Publication No. | Date | Inventor | Class |
|---|---|---|---|
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161249 A1 | 7/2006 | Realyvasquez et al. | 623/2.11 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |
| 2007/0191928 A1* | 8/2007 | Rolando et al. | 623/1.15 |

FOREIGN PATENT DOCUMENTS

| | | |
|---|---|---|
| EP | 0 466 518 | 1/1992 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |
| WO | WO 2004/082537 | 9/2004 |
| WO | WO 2004/082538 | 9/2004 |
| WO | WO 2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/103223 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |
| WO | WO 2005/000152 | 1/2005 |
| WO | WO 2005/002424 | 1/2005 |
| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |
| WO | WO 2005/018507 | 3/2005 |
| WO | WO 2005/021063 | 3/2005 |
| WO | WO 2005/023155 | 3/2005 |
| WO | WO 2005/025644 | 3/2005 |
| WO | WO 2005/027790 | 3/2005 |
| WO | WO 2005/027797 | 3/2005 |
| WO | WO 2005/034812 | 4/2005 |
| WO | WO 2005/039428 | 5/2005 |
| WO | WO 2005/039452 | 5/2005 |
| WO | WO 2005/046488 | 5/2005 |
| WO | WO 2005/046528 | 5/2005 |
| WO | WO 2005/046529 | 5/2005 |
| WO | WO 2005/046530 | 5/2005 |
| WO | WO 2005/046531 | 5/2005 |
| WO | WO 2005/048883 | 6/2005 |
| WO | WO 2005/049103 | 6/2005 |
| WO | WO 2005/051226 | 6/2005 |
| WO | WO 2005/055811 | 6/2005 |
| WO | WO 2005/055883 | 6/2005 |
| WO | WO 2005/058206 | 6/2005 |
| WO | WO 2005/065585 | 7/2005 |
| WO | WO 2005/065593 | 7/2005 |
| WO | WO 2005/065594 | 7/2005 |
| WO | WO 2005/070342 | 8/2005 |
| WO | WO 2005/070343 | 8/2005 |
| WO | WO 2005/072654 | 8/2005 |
| WO | WO 2005/072655 | 8/2005 |
| WO | WO 2005/079706 | 9/2005 |
| WO | WO 2005/082288 | 9/2005 |
| WO | WO 2005/082289 | 9/2005 |
| WO | WO 2005/084595 | 9/2005 |
| WO | WO 2005/087139 | 9/2005 |
| WO | WO 2005/087140 | 9/2005 |
| WO | WO 2006/000763 | 1/2006 |
| WO | WO 2006/000776 | 1/2006 |
| WO | WO 2006/002492 | 1/2006 |

| | | | | | | |
|---|---|---|---|---|---|---|
| WO | WO 2006/004679 | 1/2006 | | WO | WO 2006/050459 | 5/2006 |
| WO | WO 2006/005015 | 1/2006 | | WO | WO 2006/050460 | 5/2006 |
| WO | WO 2006/009690 | 1/2006 | | WO | WO 2006/054107 | 5/2006 |
| WO | WO 2006/011127 | 2/2006 | | WO | WO 2006/054930 | 5/2006 |
| WO | WO 2006/012011 | 2/2006 | | WO | WO 2006/055982 | 5/2006 |
| WO | WO 2006/012013 | 2/2006 | | WO | WO 2006/060546 | 6/2006 |
| WO | WO 2006/012038 | 2/2006 | | WO | WO 2006/063108 | 6/2006 |
| WO | WO 2006/012068 | 2/2006 | | WO | WO 2006/063181 | 6/2006 |
| WO | WO 2006/012322 | 2/2006 | | WO | WO 2006/063199 | 6/2006 |
| WO | WO 2006/019498 | 2/2006 | | WO | WO 2006/064490 | 6/2006 |
| WO | WO 2006/026371 | 3/2006 | | WO | WO 2006/065212 | 6/2006 |
| WO | WO 2006/026377 | 3/2006 | | WO | WO 2006/065930 | 6/2006 |
| WO | WO 2006/026912 | 3/2006 | | WO | WO 2006/066148 | 6/2006 |
| WO | WO 2006/027499 | 3/2006 | | WO | WO 2006/066150 | 6/2006 |
| WO | WO 2006/028821 | 3/2006 | | WO | WO 2006/069094 | 6/2006 |
| WO | WO 2006/029062 | 3/2006 | | WO | WO 2006/070372 | 7/2006 |
| WO | WO 2006/031436 | 3/2006 | | WO | WO 2006/073628 | 7/2006 |
| WO | WO 2006/031469 | 3/2006 | | WO | WO 2006/076890 | 7/2006 |
| WO | WO 2006/032051 | 3/2006 | | | | |
| WO | WO 2006/034245 | 3/2006 | | | | |
| WO | WO 2006/035415 | 4/2006 | | | | |
| WO | WO 2006/041505 | 4/2006 | | | | |
| WO | WO 2006/044679 | 4/2006 | | | | |
| WO | WO 2006/048664 | 5/2006 | | | | |

OTHER PUBLICATIONS

US 6,723,117, 04/2004, Menz et al. (withdrawn)

* cited by examiner

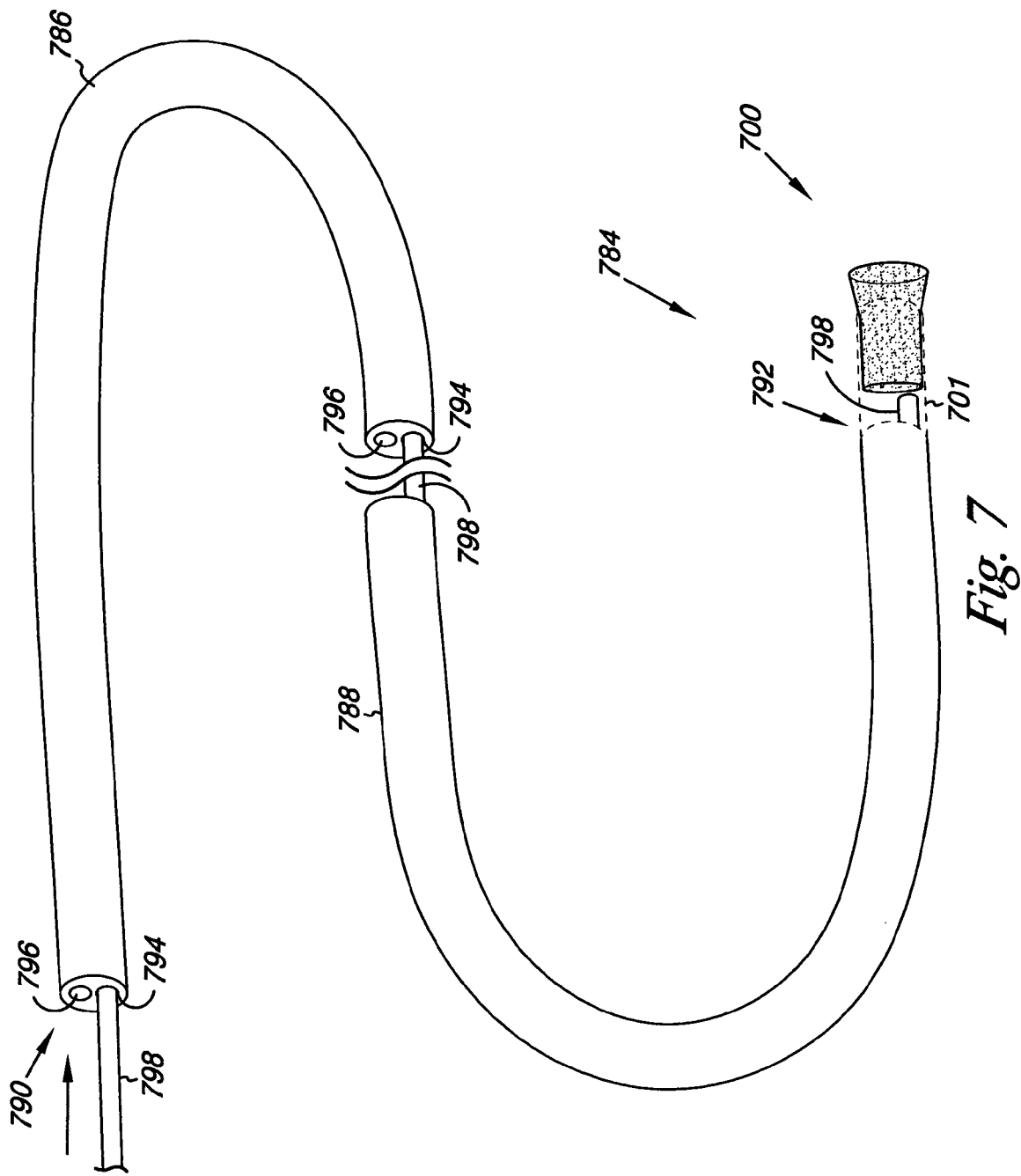

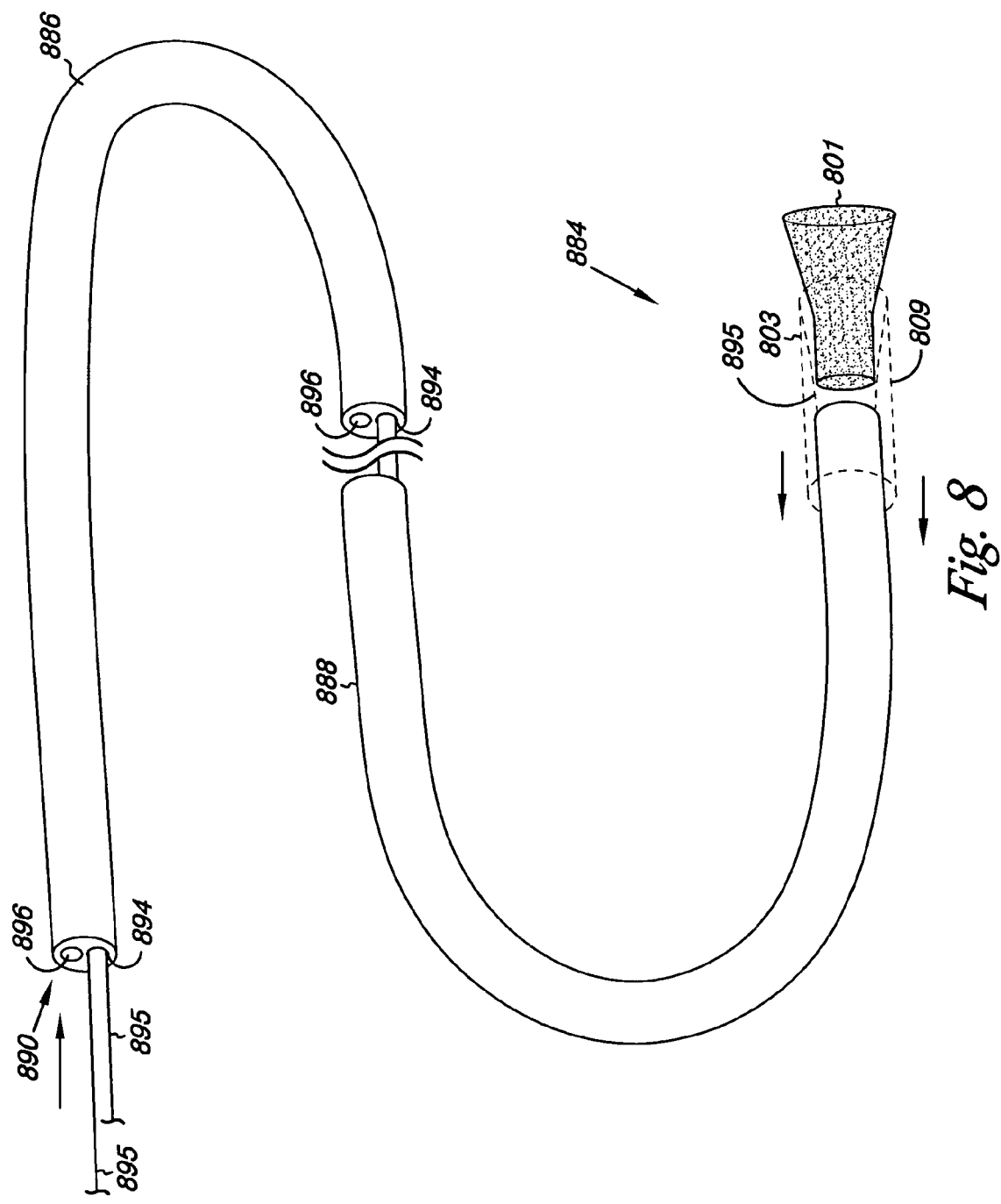

VENOUS VALVE APPARATUS, SYSTEM, AND METHOD

FIELD OF THE INVENTION

The present invention relates generally to apparatus, systems, and methods for use in a lumen; and more particularly to a valve apparatus, systems, and methods for use in the vasculature system.

BACKGROUND OF THE INVENTION

The venous system of the legs uses valves and muscles as part of the body's pumping mechanism to return blood to the heart. Venous valves create one way flow to prevent blood from flowing away from the heart. When valves fail, blood can pool in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuloplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site. Prosthetic valves can be transplanted into the venous system, but current devices are not successful enough to see widespread usage.

BRIEF DESCRIPTION OF THE DRAWINGS

FIG. 7 illustrates an embodiment of a system that includes a valve.
FIG. 8 illustrates an embodiment of a system that includes a valve.

DETAILED DESCRIPTION

Figure 1:
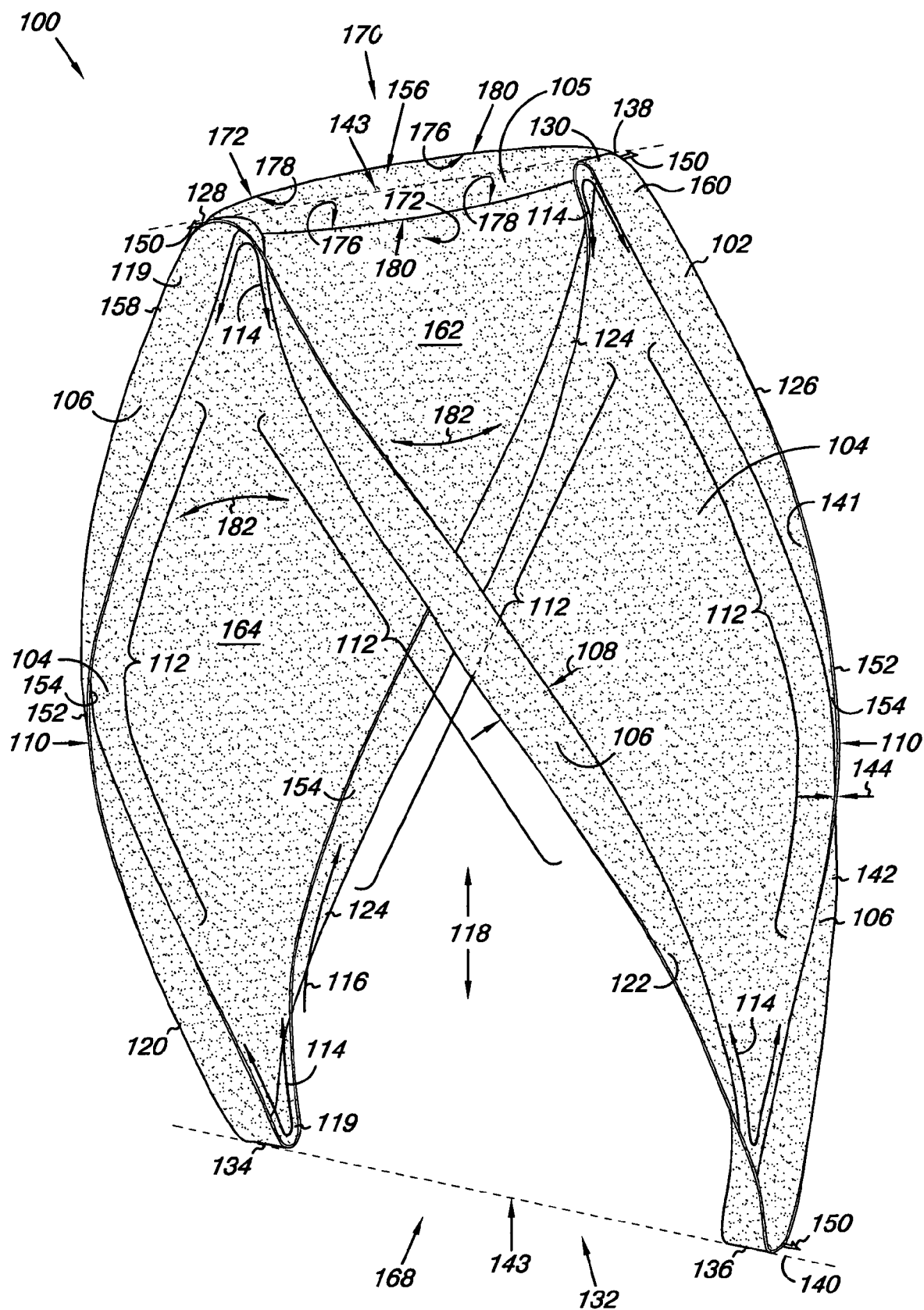
FIG. 1 illustrates an embodiment of a valve.

Embodiments of the present invention are directed to an apparatus, system, and method for valve replacement or augmentation. For example, the apparatus can include a valve that can be used to replace or augment an incompetent valve in a body lumen. Embodiments of the valve can include a frame and cover that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs.

The Figs. herein follow a numbering convention in which the first digit or digits correspond to the drawing Fig. number and the remaining digits identify an element or component in the drawing. Similar elements or components between different Figs. may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Fig. can also apply to the element shown in one or more additional Figs.

Figure 2:
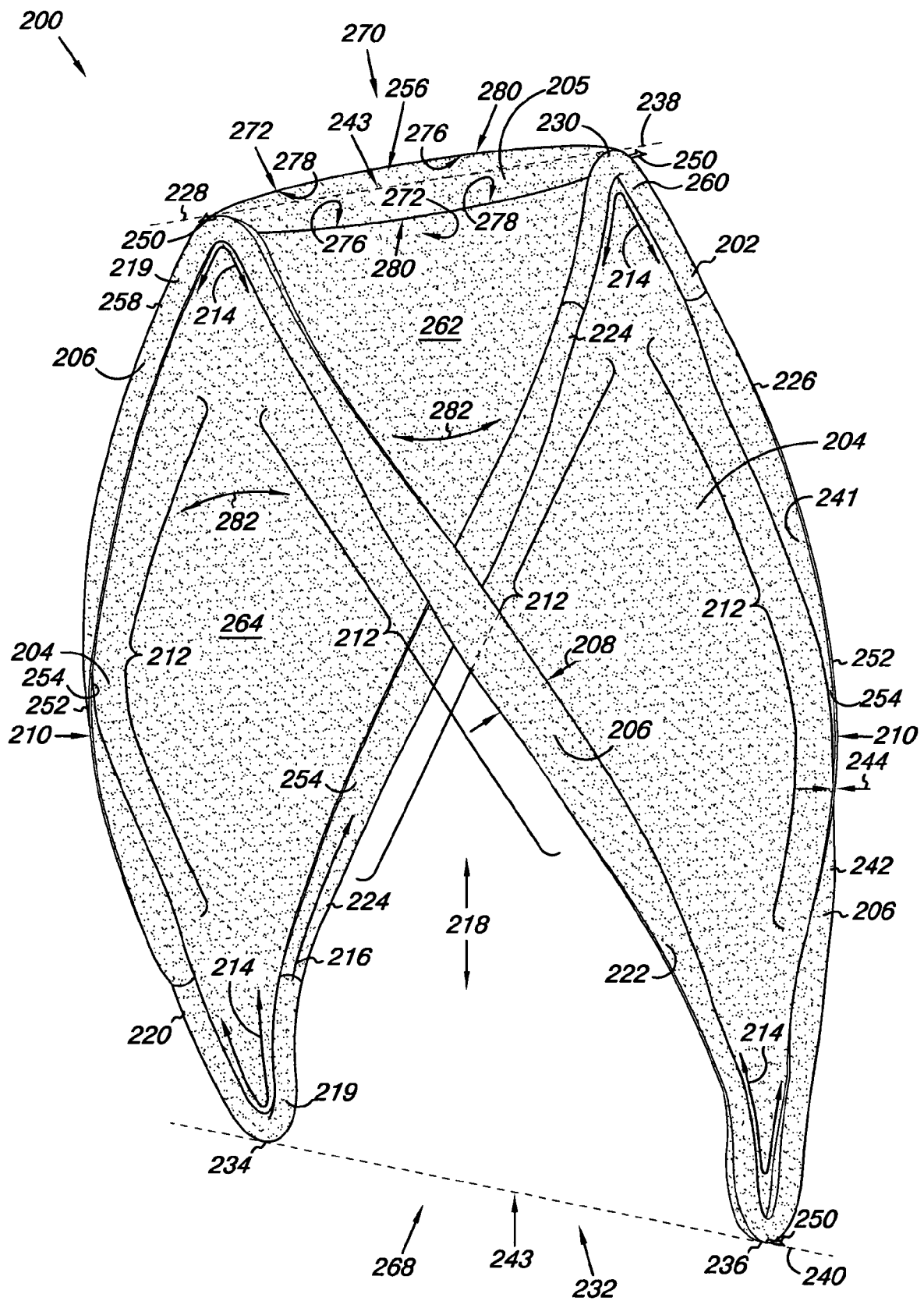
FIG. 2 illustrates an embodiment of a valve.
Figure 3:
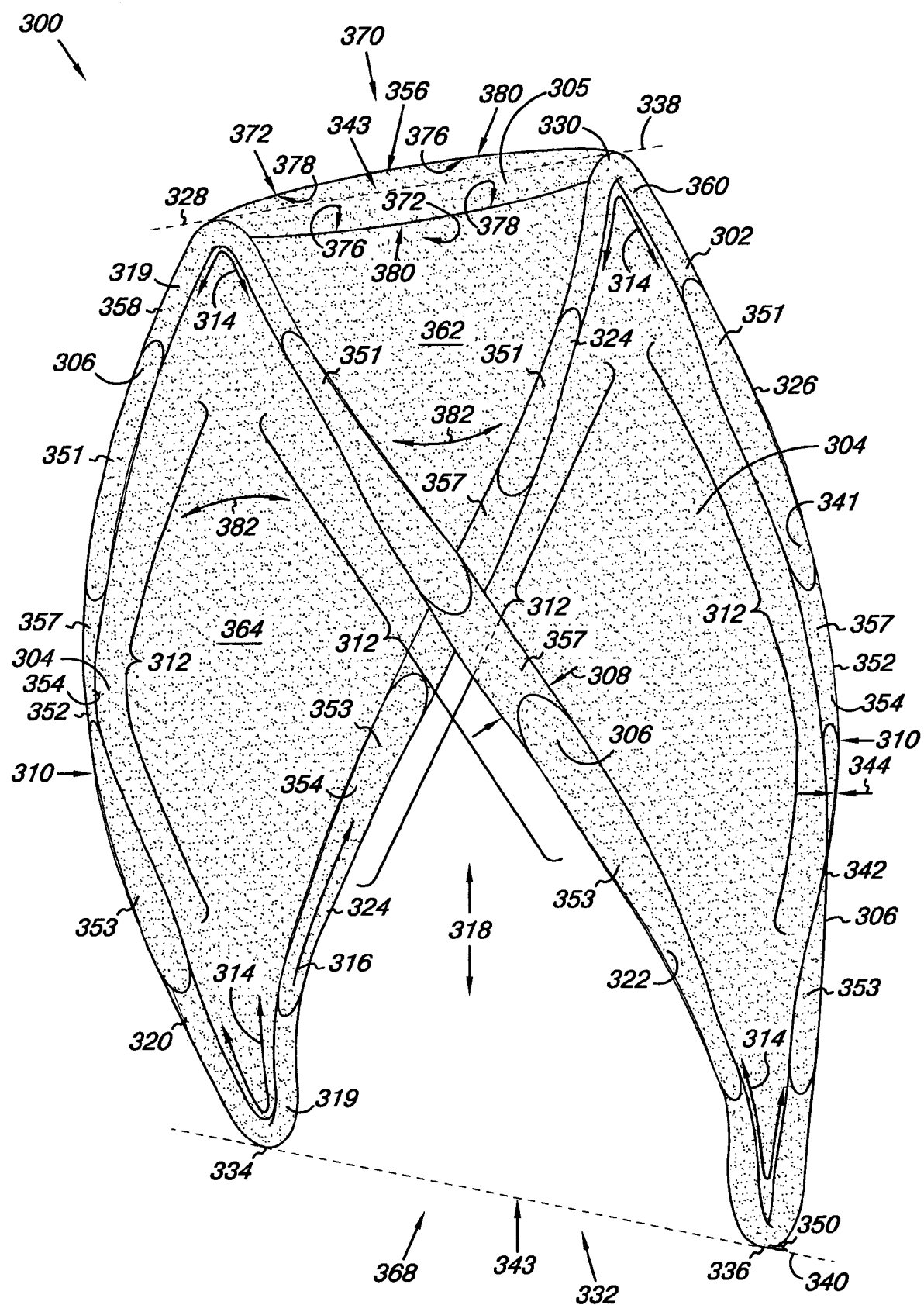
FIG. 3 illustrates an embodiment of a valve.

FIGS. 1-3 provide illustrations of various embodiments of a valve of the present invention. Generally, the valve can be implanted within the fluid passageway of a body lumen, such as for replacement or augmentation of a valve structure within the body lumen (e.g., a venous valve). In one embodiment, the valve of the present invention may be beneficial to regulate the flow of a bodily fluid through the body lumen in a single direction.

FIG. 1 illustrates one embodiment of a venous valve 100. Venous valve 100 includes a frame 102 and a cover 104 for the venous valve 100, where both the frame 102 and the cover 104 can resiliently radially collapse and expand, as will be discussed herein. Among other things, the frame 102 and the cover 104 define a lumen 105 of the valve 100. Lumen 105 allows for, amongst other things, fluid to move through the valve 100.

The frame 102 of valve 100 can have a number of configurations. For example, in the various embodiments the frame 102 can include at least a first planar surface 106 having a predetermined width 108. In one embodiment, the first planar surface 106 extends along the entire length of the frame 102, as illustrated in the embodiment of FIG. 1. In an additional embodiment, the first planar surface 106 can be present along one or more predetermined portions of the frame 102, as illustrated in FIGS. 2 and 3.

As illustrated in FIGS. 1-3, the first planar surface 106 provides an essentially flat surface defining an outer diameter 110 of the frame 102. In the various embodiments, the predetermined width 108 of the first planar surface 106 can include a number of values. As will be appreciated, the predetermined width 108 can be determined based on the location in which the venous valve 100 is to be implanted.

The predetermined width 108 of the frame 102, in addition, can have a uniform value over the length of frame 102. Alternatively, the predetermined width 108 of the frame 102 can have predetermined variations over the length of the frame 102. For example, the predetermined width 108 can be larger (i.e., wider) along one or more intermediate portions 112 of the frame 102 as compared to corner portions 114 of the frame 102. The exact configuration and values for the predetermined width 108 can depend on many patient factors, including, but not limited to, where the valve 100 is to be implanted and the physiological environment in which the valve 100 is to be implanted.

In addition, the intermediate portions 112 of the frame 102 can further include at least a partial helical configuration 116. For example, the first planar surface 106 of frame 102 can follow the partial helical configuration 116 extending along a longitudinal central axis 118 of the frame 102 such that the first planar surface 106 maintains an essentially symmetrical relation to the outer diameter 110 of the frame 102. In one embodiment, this configuration of the frame 102 allows the first planar surface 106 along the intermediate portions 112 to essentially follow along a tubular shaped path extending along the longitudinal central axis 118. In other words, the first planar surface 106 rotates (e.g., twists) as it extends along the longitudinal central axis 118 to essentially track the tubular (e.g., circular) surface along points that cross right sections of the tubular surface at an oblique angle. In addition, this configuration of the frame 102 can further allow the first planar surface 106 to essentially follow the tubular (e.g., circular) path as the frame 102 moves between a compressed and expanded state, as will be more fully discussed herein.

In the various embodiments described herein, the corner portions 114 of the frame 102 can provide a spring force to counter radial compression of the frame 102. As will be appreciated, additional spring force can be imparted to the frame 102 from the compression of the partial helical configuration 116 of the intermediate portions 112 of the frame 102 as well. For example, as all or a portion of the frame 102 is radially compressed towards the longitudinal central axis 118, both the corner portions 114 and the partial helical configuration 116 of the frame 102 can resiliently bend (e.g., the spiral shape of the partial helical configuration is turned more tightly) to store elastic force (e.g., elastic potential energy) that allows the frame 102 to expand radially so as to return towards its uncompressed state.

As illustrated in FIG. 1, the first planar surface 106 of the frame 102 can turn from its essentially symmetrical relation to the outer diameter 110 of the frame 102 to form one embodiment of the corner portions 114. So, for example, in FIG. 1 the first planar surface 106 forms an inner surface 119 of the corner portion 114. In an alternative embodiment, the first planar surface 106 of the frame 102 includes an essentially symmetrical relation to the outer diameter 110 of the frame 102 through the corner portions 114. An example of this embodiment is provided in FIGS. 2 and 3.

As illustrated in FIGS. 1-3, the frame 102 can be described as having a first member 120, a second member 122, a third member 124, and a fourth member 126. As illustrated in FIGS. 1-3, each of the first, second, third, and fourth member 120, 122, 124, and 126, each include at least the first planar surface 106. In addition, the corner portions 114 of the frame 102 provide a first vertex 128 and a second vertex 130 relative a first end 132 of the frame 102, and a third vertex 134 and a fourth vertex 136 relative the first and second vertices 128 and 130. In one embodiment, the first vertex 128 and the second vertex 130 are positioned opposite each other along a first common axis 138. Similarly, the third vertex 134 and the fourth vertex 136 are positioned opposite each other along a second common axis 140. Other relative positions for the vertices 128, 130, 134, and 136 are also possible.

As illustrated in FIGS. 1-3, the first member 120 and the second member 122 extend from the first vertex 128, and the third member 124 and the fourth member 126 extend from the second vertex 130. Similarly, the first member 120 and the third member 124 extend from the third vertex 134 at the first end 132 of the frame 102 relative the first and second vertices, 128 and 130, and the second member 122 and the fourth member 126 extend from the fourth vertex 136 at the first end 132 of the frame 102 relative the first and second vertices 128 and 130.

In the various embodiments, the frame 102 can provide symmetrical relationships for the members 120, 122, 124 and 126 and the vertices 128, 130, 134 and 136. For example, as illustrated in FIGS. 1-3 the frame 102 can provide both bilateral symmetry and radial symmetry, among other things. With respect to bilateral symmetry, the second member 122 and the fourth member 126 can have a symmetrical relationship to the first member 120 and the third member 124, respectively, across a plane extending from the first common axis 138 and bisecting the second common axis 140 perpendicularly. In other words, the second member 122 and the fourth member 126 can provide a mirror image of the first member 120 and the third member 124, respectively. Similarly, the first vertex 128 and the third vertex 134 can provide mirror images of the second vertex 130 and the fourth vertex 136, respectively.

In additional embodiments, the frame 102 can also provide radial symmetry for the members 120, 122, 124 and 126 and the vertices 128, 130, 134 and 136. For example, FIGS. 1-3 provide an illustration of radial symmetry for the members 120, 122, 124 and 126 and the vertices 128, 130, 134 and 136 around the longitudinal central axis 118 of the frame 102. As illustrated, the first member 120 and the second member 122 can be positioned approximately ninety (90) degrees relative each other around the longitudinal central axis 118 of the frame 102. Similarly, the second member 122 and the fourth member 126, the third member 124 and the fourth member 126, and the third member 124 and the first member 120 can be positioned approximately ninety (90) degrees relative each other around the longitudinal central axis 118 of the frame 102.

As will be appreciated, the various members and vertices of the frame 102 need not necessarily, however, display a symmetrical relationship in order to practice the embodiments of the present invention. For example, in an additional embodiment the radial relationship of the first member 120 and the second member 122 can be set apart approximately ninety (90) degrees or greater relative each other around the longitudinal central axis 118 of the frame 102. In which case the first member 120 and the third member 124, and the second member 122 and the fourth member 126 can be set apart approximately ninety (90) degrees or less relative each other around the longitudinal central axis 118 of the frame 102. Other radial relationships are also possible.

As illustrated in FIGS. 1-3, the frame 102 can have similar and/or different cross-sectional geometries along its length. The similarity and/or the differences in the cross-sectional geometries can be based on one or more desired functions to be elicited from each portion of the frame 102 (e.g., the members 120, 122, 124, 126, and the vertices 128, 130, 134 and 136).

For example, the frame 102 can have a similar cross-sectional geometry along its length. FIG. 1 provides an illustration of the similar cross-sectional geometry, where the frame 102 includes a second planar surface 141 interior to the frame 102 and parallel with the first planar surface 106 so as to provide a strip 142 of material to form the frame 102. The strip 142 of material forming the frame 102 includes a dimension of height 144 between the first planar surface 106 and the second planar surface 141 so as to provide an aspect ratio of the predetermined width 108 to the height 144. As will be appreciated, the aspect ratio can have one or more values that provide the frame 102 with sufficient strength, flexibility and/or rigidity for the environment, including the physical demands, in which the venous valve 100 is to be used. Embodiments of the invention are not so limited.

Alternatively, the frame 102 can include portions having the first planar surface 106 with the other portions of the frame 102 surfaces having a non-planar configuration. For example, FIGS. 2 and 3 illustrate embodiments in which the frames 202 and 302 have different cross-sectional geometries along their length. For example, FIG. 2 provides an illustration in which the corner portions 214 of the frame 202, including the vertices 228, 230, 234 and 236, can have one or more of a semi-round (e.g., semi-circular, semi-oval, and/or semi-elliptical) cross-sectional geometry, while the members 220, 222, 224, and 226 can have a strip 242 geometry, as described herein. As will be appreciated, each of the corner portions 214 of the frame 202 can themselves have similar and/or different cross-sectional geometries (e.g., corner portions 214 of vertices 228 and 230 could have a semi-circular cross-sectional geometry, while the corner portions 214 of vertices 234 and 236 could have a semi-elliptical cross-sectional geometry). Other combinations of cross-sectional geometries are possible.

Figure 4A:
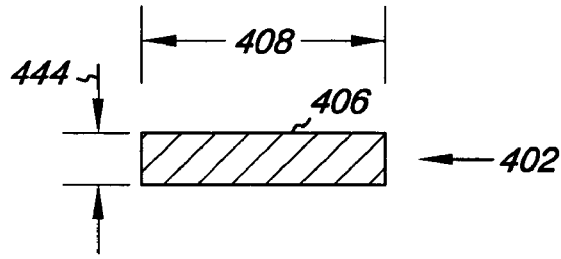
FIGS. 4A-4F illustrate embodiments of cross-sectional geometries for use with embodiments of a valve.
Figure 4B:
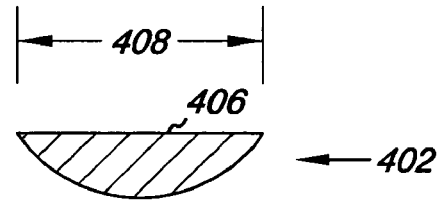
Figure 4C:
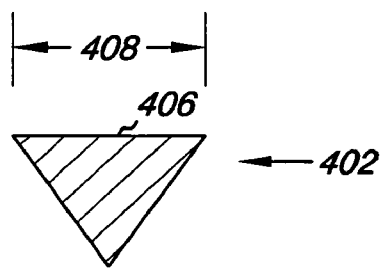
Figure 4D:
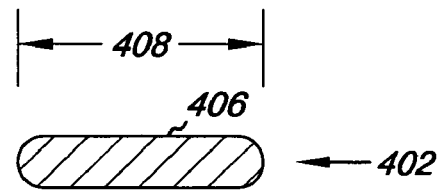
Figure 4E:
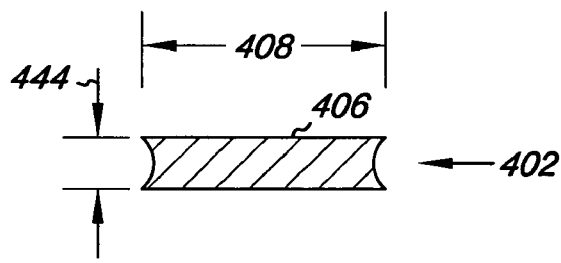
Figure 4F:
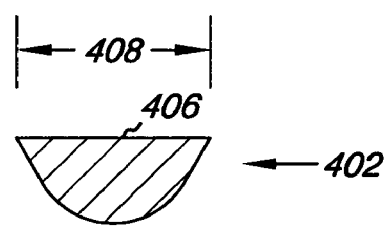

While the members 220, 222, 224, and 226 are illustrated herein as having a planar cross-sectional configuration, other configurations are also possible. For example, FIGS. 4A-4F provide non-limiting examples cross-sectional geometries for one or more portions of the members 220, 222, 224, and 226, and the corner portions 214 of the frame 202. As shown in FIGS. 4A-4F, examples of cross-sectional geometries include, but are not limited to, rectangular geometries having perpendicular sides (FIG. 4A), one or more convex sides (FIG. 4D), and one or more concave sides (FIG. 4E), semi-circular (FIGS. 4B and 4F) and triangular (FIG. 4C). Additional examples of cross-sectional geometries for one or more portions of the frame 202 include, but are not limited to, circular, tubular, I-shaped, T-shaped, oval, and trapezoidal.

FIG. 3 provides an additional embodiment of frame 302 having different cross-sectional geometries along its length. For example, FIG. 3 provides an illustration in which the corner portions 314 of the frame 302, including the vertices 328, 330, 334 and 336, can have one or more of a round (e.g., circular, oval, and/or elliptical) cross-sectional geometry. As will be appreciated, each of the corner portions 314 of the frame 302 can themselves have similar and/or different cross-sectional geometries (e.g., corner portions 314 of vertices 328 and 330 could have a circular cross-sectional geometry, while the corner portions 314 of vertices 334 and 336 could have a elliptical or semi-elliptical cross-sectional geometry). Other combinations of cross-sectional geometries are possible.

In addition, FIG. 3 provides an illustration in which one or more of the intermediate portions 312 of the frame 302 can have different cross-sectional shapes along their length. For example, one or more of the members 320, 322, 324, and 326 can have a strip 342 geometry along a first length 351 and a second length 353 of the intermediate portion 312, and a round and/or semi-round (as discussed herein) 355 geometry along a third length 357 of the intermediate portion 312. As will be appreciated, various combinations of the cross-sectional geometries, as discussed herein, along the first, second, and third lengths 351, 353, and 357 are possible.

In addition to changes in cross-sectional geometry, there can also be changes in the widths 308 and/or the diameters of the round and/or semi-round geometries relative to each other along the length of the frame 302. Changes in shapes, cross-sectional geometries, widths and/or diameters can depend on many patient factors, including, but not limited to, where the valve 300 is to be implanted and the physiological environment in which the valve 300 is to be implanted.

As will be appreciated, the embodiments discussed herein are not intended to limit the present invention, as it is appreciated that other cross-sectional geometries and combinations thereof are also possible. As such, the present invention should not be limited to the illustration of the frame 102 in FIG. 1, the frame 202 in FIG. 2 and/or frame 302 in FIG. 3. In addition, transitions from one cross-sectional geometry to another cross-sectional geometry (e.g., from a round cross-sectional geometry to a ribbon cross-sectional geometry) can be created by mechanically deforming (e.g., with rollers or a press) the frame material. Other mechanisms for deforming the cross-sectional shape of the frame are also possible.

Referring again to FIGS. 1-3, the outer diameter 110, 210, and 310 and a length 143, 243, and 343 of valves 100, 200, and 300, respectively, can have a number of values. As will be appreciated, the outer diameter 110, 210, and 310 and the length 143, 243, and 343 of valves 100, 200, and 300, can each be determined based upon the location into which the valve 100, 200, and 300 is to be implanted.

Referring now to FIG. 1, the portions of frame 102 (e.g., the corner portions 114 and/or the intermediate portions 112) can further provide elastic regions for the frame 102. Typically, these elastic regions occur at portions of the frame 102 that include the curves and twists in the frame 102. The elastic regions allow the valve 100 to accommodate changes in body lumen size (e.g., diameter of the body lumen) by flexing to expand and/or contract to change the diameter of the frame 102. In one embodiment, the corner portions 114 and/or the intermediate portions 112 of the frame 102 can act as springs to allow the valve 100 to resiliently radially collapse and expand. The frame 102 can also provide sufficient contact and expansion force with the surface of a body lumen wall to encourage fixation of the valve 100 and to prevent retrograde flow within the body lumen around the edges of the frame 102 and the surface of a lumen when combined with a closed state of the valve leaflets (described in more detail below) attached thereto. Anchoring elements (e.g., barbs) can also be included with valve 100, as will be discussed herein.

Figure 5B:
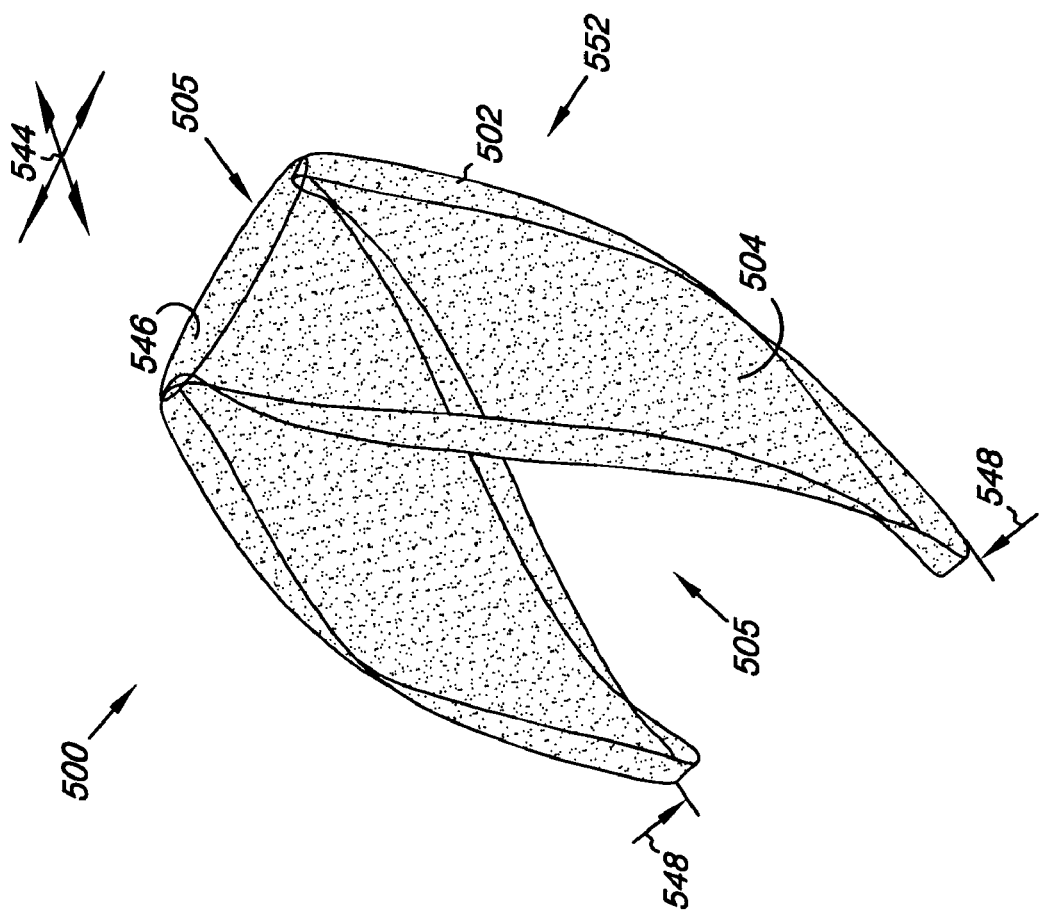
FIGS. 5A-5B illustrate a valve in an expanded and collapsed state.
Figure 5A:
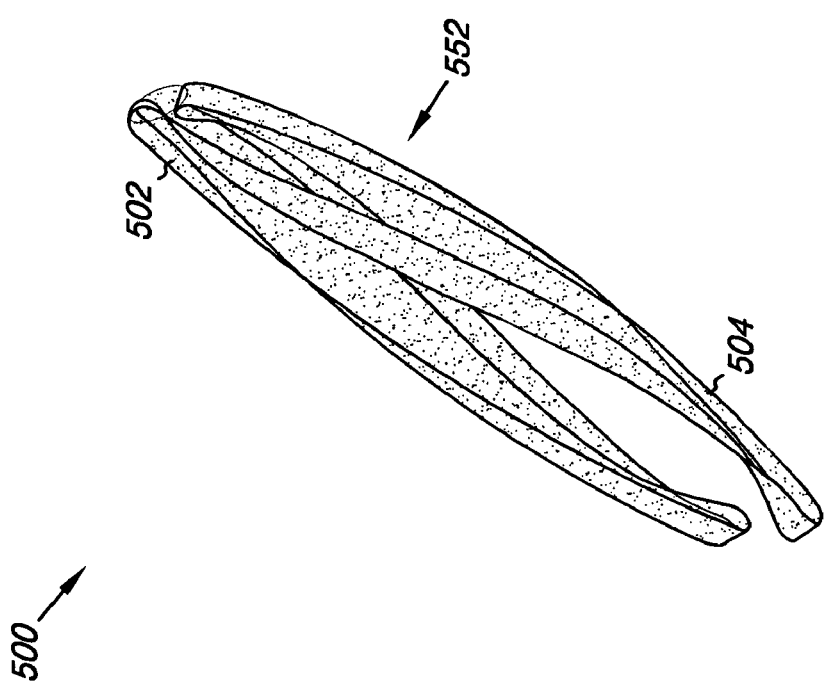

The elastic regions of the frame 102 also allow valve 100 to elastically and repeatably travel between a collapsed state and an expanded state. FIGS. 5A and 5B provide an example of the valve 500 in a collapsed state (FIG. 5A) and in an expanded state (FIG. 5B). As shown in FIGS. 5A and 5B, the valve 500 can travel between the collapsed and the expanded state along a radial travel path 544 (as shown in FIG. 5B), where there can be a change in a cross sectional area 546 of lumen 505. For example, the valve frame 502 can travel along the radial travel path 544 so as to change a width 548 of lumen 505. This can allow the valve 500 to react appropriately to the distension and contraction of a body lumen in which the valve 500 is placed.

In addition to the illustrated corner portions 114, the elastic regions can further include, but are not limited to, other shapes for the valve frame 102 that allow for repeatable travel between the collapsed state and the expanded state. For example, the elastic regions can include integrated springs having a circular or an elliptical loop configuration. Other shapes are also possible.

The embodiments of the frame, such as frame 102 in FIG. 1, frame 202 in FIG. 2 and frame 302 in FIG. 3, can also be constructed of one or more of a number of materials and in a variety of configurations. Generally, the frame embodiments can have a unitary structure with an open frame configuration. The frame can also be self-expanding. Examples of self-expanding frames include those formed from temperature-sensitive memory alloy which changes shape at a designated temperature or temperature range. Alternatively, the self-expanding frames can include those having a spring-bias. In addition, the frame 102, 202, 302 can have a configuration that allows the frame embodiments be radially expandable through the use of a balloon catheter.

The materials used in constructing frame embodiments can also be pre- and post-treated. For example, the material characteristics of the frame can be modified by imparting to the corner portions, e.g. 114, 214 and 314, a radial arc that flares the frame outward from the longitudinal central axis. In one embodiment, the radial arc may be sufficiently large such that portions of the frame at the corners may extend beyond the outer diameter of the frame as defined by the first planar surface. Illustrations of such a radial arc, such as those described herein, can be found in co-pending U.S. patent application Ser. No. 11/150,331, filed on Jun. 10, 2005 and entitled "Venous Valve Frame, System, and Method", which is incorporated herein by reference in its entirety.

The embodiments of the frame, such as frame 102 in FIG. 1, frame 202 in FIG. 2, and frame 302 in FIG. 3, can also be formed from one or more contiguous frame members. For example, the frame member of frame embodiments can be a single contiguous member. The single contiguous member can be bent around an elongate tubular mandrel to form the frame. The free ends of the single contiguous member can then be welded, fused, crimped, or otherwise joined together to form the frame. For example, the free ends of the single contiguous member could be joined through a butt joint. In addition, a joint could further include a collar, such as a segment of hypo tubing, place over and secured with the butt joint. In an additional embodiment, the frame member of frame can be derived (e.g., laser cut, water cut) from a single tubular segment. In an alternative embodiment, methods of joining the frame member to create the elastic region include, but are not limited to, welding, gluing, and fusing the frame member. The frame can be heat set by a method as is typically known for the material which forms the frame.

The frame embodiments can be formed from a number of materials. For example, the frame can be formed from a biocompatible metal, metal alloy, polymeric material, or combination thereof. As discussed herein, the frame can be self-expanding or balloon expandable. In addition, the frame can be configured so as to have the ability to move radially between the collapsed state and the expanded state. To accomplish this, the material used to form the frame should exhibit an elastic modulus and a yield stress that can accommodate large elastic strains and can recover from elastic deformations. Examples of suitable materials include, but are not limited to, medical grade stainless steel (e.g., 316L), titanium, tantalum, platinum alloys, niobium alloys, cobalt alloys, alginate, or combinations thereof. Additional frame embodiments may be formed from a shape-memory material, such as shape memory plastics, polymers, and thermoplastic materials which are inert in the body. Shaped memory alloys having superelastic properties generally made from ratios of nickel and titanium, commonly known as nitinol, are also possible materials. Other materials are also possible.

Frame can be expanded to provide a lumen (e.g., 105 in FIG. 1, 205 in FIG. 2, and 305 in FIG. 3) having a number of sizes. For example, the size of the lumen can be determined based upon the type of body lumen and the body lumen size in which the valve is to be placed. In an additional example, there can also be a minimum value for the width for the frame that ensures that the frame will have an appropriate expansion force against the inner wall of the body lumen in which the valve is being placed.

In one embodiment, the frame can further include one or more anchoring elements. For example, the one or more anchoring elements can include, but are not limited to, one or more barbs 150 projecting from the frame 102. The valve can further include one or more radiopaque markers (e.g., tabs, sleeves, welds, coatings such as formed by plating or dipping). For example, one or more portions of the frame can be formed from a radiopaque material. Radiopaque markers can be attached to and/or coated onto one or more locations along the frame. Examples of radiopaque material include, but are not limited to, gold, tantalum, and platinum. The position of the one or more radiopaque markers can be selected so as to provide information on the position, location and orientation of the valve during its implantation.

The embodiments of the valve further include the cover. In one embodiment, cover 104 can be located over at least the first planar surface 106 of the frame 102 so as to cover at least part of an outer surface 152 of the frame 102. For example, the cover 104 can extends over the outer surface 152 of the frame 102 so as to cover the outer surface 152 of the frame 102 thereby limiting, or eliminating, the exposure of the outer surface 152 of the frame 102.

In an additional example, the cover 104 can extend between each of the members 120, 122, 124, and 126 and vertices 128, 130, 134 and 136 to surround the circumference of the frame 102. Examples of are generally illustrated in FIGS. 1-3, 5 and 6. In an additional embodiment, the cover 104 can also be located over at least an inner surface 154 of the frame 102. A further embodiment includes the cover 104 located over at least the outer surface 152 and the inner surface 154. The cover 104 can further include surfaces defining a reversibly sealable opening 156 for unidirectional flow of a liquid through the lumen 105. For example, the surfaces of the cover 104 can be deflectable between a closed configuration in which fluid flow through the lumen 105 can be restricted and an open configuration in which fluid flow through the lumen 105 can be permitted.

Figure 6A:
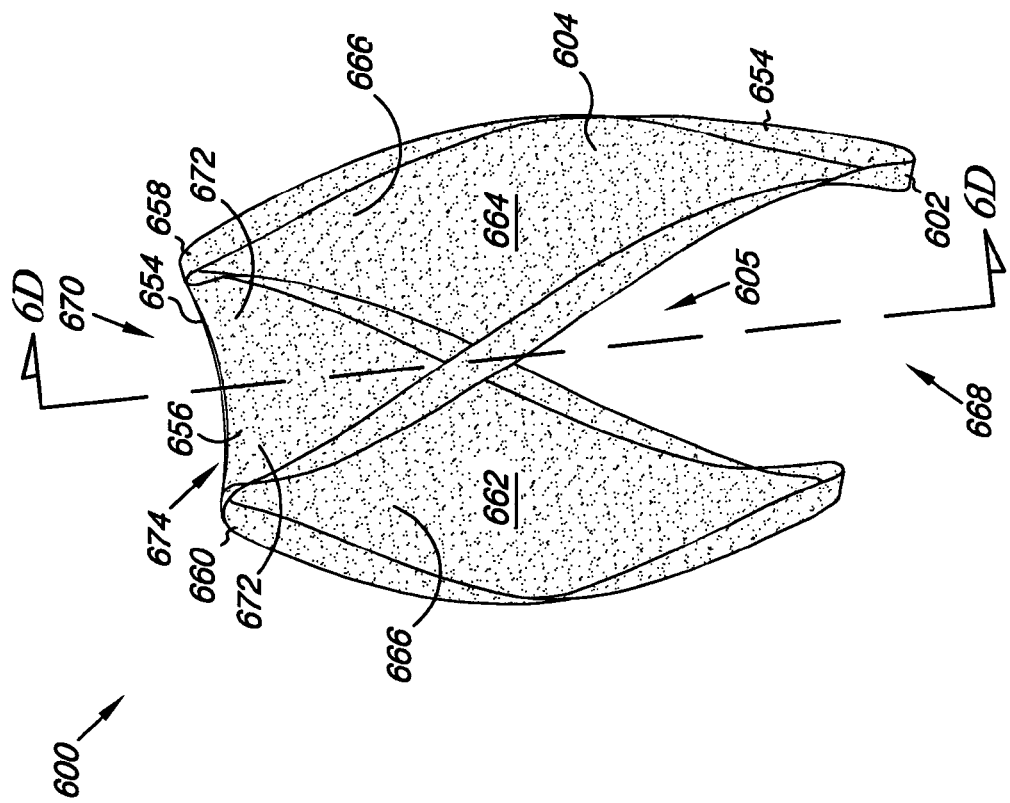
FIGS. 6A-6D illustrate an embodiment of a valve.
Figure 6B:
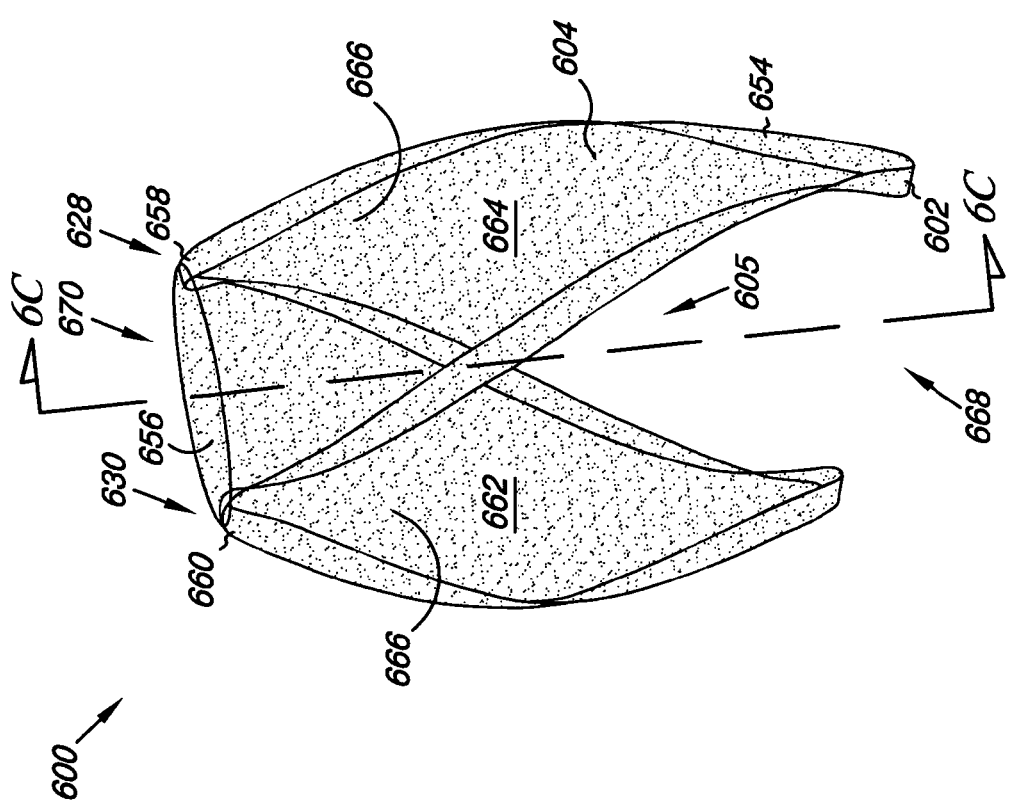
Figure 6C:
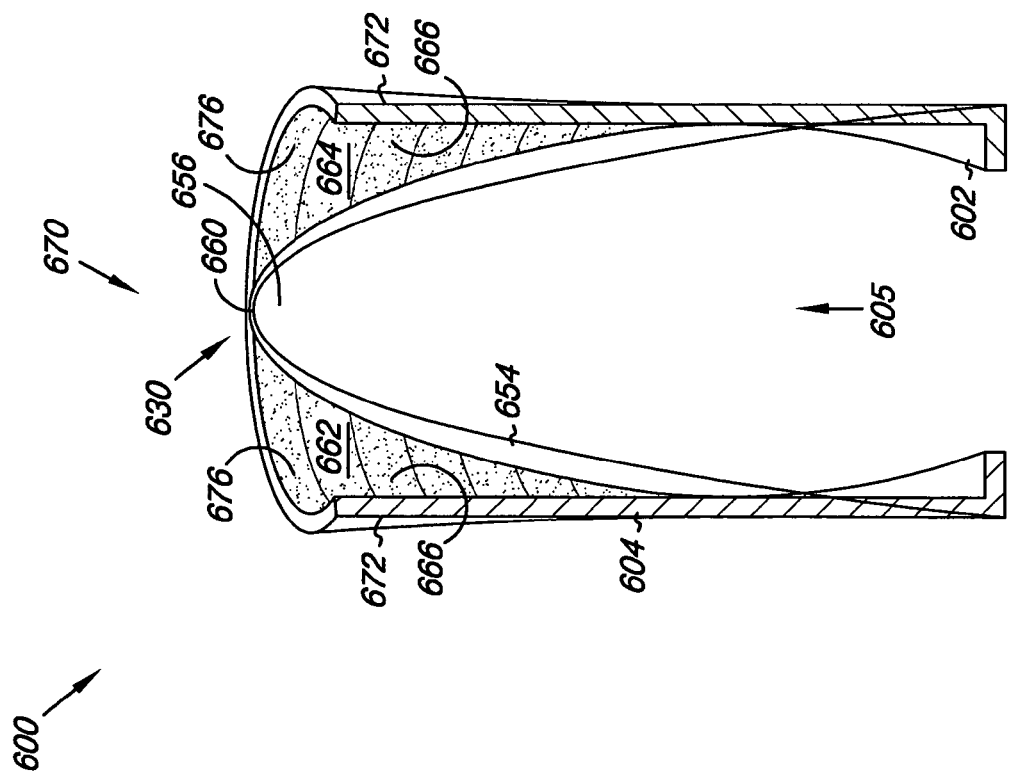
Figure 6D:
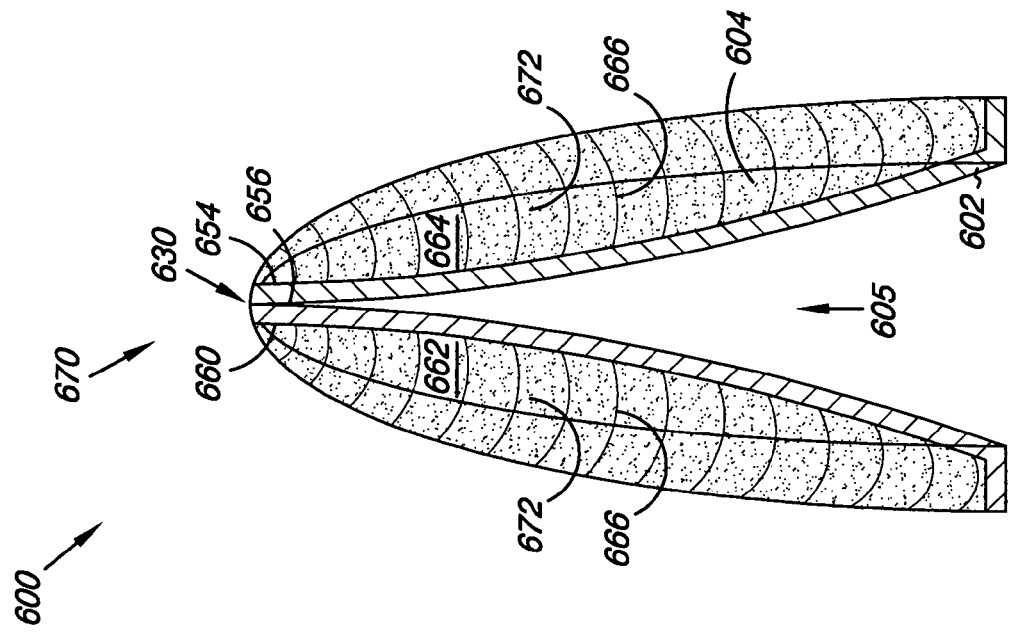

FIGS. 6A-6D illustrate an additional embodiment of the venous valve 600. FIGS. 6A and 6B provide a perspective illustration of valve 600 in an open configuration (FIG. 6A) and a closed configuration (FIG. 6B). FIGS. 6C and 6D provide a sectional view taken along cut lines 6C-6C and 6D-6D shown in FIGS. 6A and 6B, respectively, to more clearly illustrate the embodiment of the venous valve 600.

As discussed herein, cover 604 includes surfaces defining the reversibly sealable opening 656 for unidirectional flow of a liquid through the lumen 605. For the embodiment illustrated in FIGS. 6A and 6B, the cover 604 extends over at least a portion of the frame 602 to a first connection point 658 and a second connection point 660 on the frame 602, as the same have been described and illustrated in connection with FIGS. 1-3. In one example, the first connection point 658 and the second connection point 660 can be located at the first vertex 628 and the second vertex 630 of the frame 602. The cover 604 extends between the first connection point 658 and the second connection point 660 to provide a first valve leaflet 662 and a second valve leaflet 664. The first valve leaflet 662 and the second valve leaflet 664 can form the reversibly sealable opening 656 extending between the first connection point 658 and the second connection point 660. So, for the example shown in FIG. 6A the first valve leaflet 662 and the second valve leaflet 664 form the reversibly sealable opening 656 extending between the first vertex 628 and the second vertex 630 of the frame 602.

As illustrated, the first valve leaflet 662 and the second valve leaflet 664 include a region 666 of the cover 604 that can move relative the frame 602. The region 666 of the cover 604 can be unbound (i.e., unsupported) by the frame 602 and extends between the first connection point 658 and the second connection point 660 of the valve 600. This configuration permits the reversibly sealable opening 656 to open and close in response to the fluid pressure differential across the valve leaflets 662 and 664.

For example, under antegrade fluid flow (i.e., positive fluid pressure) from a first end 668 towards a second end 670 of the valve 600, the first and second valve leaflets 662 and 664 can expand toward the inner surface 654 to create an opening through which fluid is permitted to move. In one example, the first valve leaflet 662 and the second valve leaflet 664 can each expand to define a semi-tubular structure when fluid opens the reversibly sealable opening 656. An example of the open configuration for the valve is shown in FIGS. 6A and 6C.

Under a retrograde fluid flow (i.e., negative fluid pressure) from the second end 670 towards the first end 668, the first and second valve leaflets 662 and 664 can move away from the inner surface 654 as the valve leaflets 662 and 664 begin to close valve 600. In one example, a pocket exists between the frame 602 and each of the first and second valve leaflets 662 and 664. The pocket allows fluid from the retrograde flow to develop pressure on a first major face 672 of the first and second valve leaflets 662 and 664, for example, as illustrated in FIG. 6D. As fluid pressure develops, the first and second valve leaflets 662 and 664 collapse, closing the reversibly sealable opening 656 to create a seal 674, thereby restricting retrograde fluid flow through the valve 600. In one example, the seal 674 can be created by the joining of a sealing surface 676 of the first and second valve leaflets 662 and 664, for example as illustrated in FIG. 6C. In the closed configuration, the first and second valve leaflets 662 and 664 can each have a concave structure when fluid closes the reversibly sealable opening 656. An example of a closed configuration for the valve is shown in FIGS. 6B and 6D.

Referring again to FIG. 1, valve 100 provides an embodiment in which the surfaces defining the reversibly sealable opening 156 provide a bi-leaflet configuration (i.e., a bicuspid valve) for valve 100. Although the embodiments in FIGS. 1, 2, 3 and 6A-6D illustrate and describe a bi-leaflet configuration for the valve of the present invention, designs employing a different number of valve leaflets (e.g., tri-leaflet valve) are possible. For example, additional connection points (e.g., three or more) could be used to provide additional valve leaflets (e.g., a tri-leaflet valve).

The first valve leaflet 162 and the second valve leaflet 164 can have a variety of sizes and shapes. For example, each of the first valve leaflet 162 and the second valve leaflet 164 can have a similar size and shape. In addition, each of the first valve leaflet 162 and the second valve leaflet 164 can include opposed first and second major surfaces 172 and 178, respectively. Each first major surface 172 of the first valve leaflet 162 and the second valve leaflet 164 can be oriented to face the second end 170 of valve 100.

Each of the first valve leaflet 162 and the second valve leaflet 164 can further provide the sealing surface 176 formed by portions of the first valve leaflet 162 and the second valve leaflet 164, where the sealing surface 176 can engage to define the closed configuration of valve 100. Sealing surface 176 of the first valve leaflet 162 and the second valve leaflet 164 can separate to provide for an open configuration of valve 100. In an additional example, each of the first valve leaflet 162 and the second valve leaflet 164 need not have a similar size and shape (i.e., the valve leaflets can have a different size and shape with respect to each other).

In one embodiment, each of the first valve leaflet 162 and the second valve leaflet 164 includes sufficient excess material spanning frame 102 such that fluid pressure (e.g., antegrade flow) acting on the second major surface 178 of the first valve leaflet 162 and the second valve leaflet 164 forces the valve 100 into an open configuration. The first valve leaflet 162 and the second valve leaflet 164 each further include an arcuate edge 180 positioned adjacent each other along a substantially catenary curve between the connection point 158 and the second connection point 160 in the closed configuration of valve 100. Similarly, the arcuate edge 180 can define opening 156 when the valve 100 is in the open configuration.

In an additional embodiment, in the open configuration the portion of the cover 104 forming the first valve leaflet 162 and the second valve leaflet 164 provides sufficient excess material spanning between the first connection point 158 and the second connection point 160 to allow the first and second major surfaces 172 and 178 to take on a semi-tubular structure 182, as shown in FIG. 1, when fluid pressure opens the valve 100. In an additional embodiment, the arcuate edges 180 of valve 100 can open to approximately the full inner diameter of a body lumen.

Each of the second major surfaces 178 of the first valve leaflet 162 and the second valve leaflet 164 can further include a curve imparted thereto so as to provide the first major surface 172 with the concave structure. The concave structure allows the first valve leaflet 162 and the second valve leaflet 164 to better collect retrograde fluid flow to urge the first valve leaflet 162 and the second valve leaflet 164 towards the closed configuration. For example, as retrograde flow begins, the first valve leaflet 162 and the second valve leaflet 164 respond by moving towards the center (e.g., towards 118) of valve 100. As the first valve leaflet 162 and the second valve leaflet 164 approach the center of the device the sealing surfaces 176 make sufficient contact to effectively close valve 100 and restrict retrograde fluid flow.

In an additional embodiment, the first valve leaflet 162 and the second valve leaflet 164 can include one or more support structures, where the support structures can be integrated into and/or onto the valve leaflets 162 and 164. For example, the first valve leaflet 162 and the second valve leaflet 164 can include one or more support ribs, as the same will be known and understood, having a predetermined shape. In one embodiment, the predetermined shape of the support ribs can include a curved bias so as to provide the first valve leaflet 162 and the second valve leaflet 164 with a curved configuration. Support ribs can be constructed of a flexible material and have dimensions (e.g., thickness, width and length) and cross-sectional shape that allows the support ribs to be flexible when the first valve leaflet 162 and the second valve leaflet 164 are urged into an open position, and stiff when the first valve leaflet 162 and the second valve leaflet 164 are urged into a closed position upon experiencing sufficient back flow pressure from the direction downstream from the valve. In an additional embodiment, support ribs can also be attached to valve frame 102 so as to impart a spring bias to the valve leaflets in either the open or the closed configuration.

In one embodiment, the material of the first valve leaflet 162 and the second valve leaflet 164 can be sufficiently thin and pliable so as to permit radially-collapsing of the valve leaflets for delivery by catheter to a location within a body lumen. The first valve leaflet 162 and the second valve leaflet 164 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethlylene (PE), polyethylene terephthalate (PET), silk, urethane, Rayon, Silicone, or the like. Possible biologic materials include, but are not limited to, autologous, allogeneic or xenograft material. These include explanted veins and decellularized basement membrane materials, such as small intestine submucosa (SIS) or umbilical vein.

As discussed herein, the cover 104 can be located over at least the outer surface 152 of the frame 102. In an additional embodiment, the cover 104 can also be located over at least the inner surface 154 of the frame 102, where the cover 104 can be joined to itself in the area between the members (e.g., between first member 120 and third member 124, and second member 122 and fourth member 128) so as to fully or partially encase the frame 102. Numerous techniques may be employed to laminate or bond cover 104 on the outer surface 152 and/or the inner surface 154 of the frame 102, including heat setting, adhesive welding, application of uniform force and other bonding techniques. Additionally, the cover 104 may be folded over the first end of the frame 102 to provide the cover 104 on both the outer surface 106 and the inner surface 108. Cover 104 can also be joined to itself and/or the members according to the methods described in U.S. Patent Application Publication US 2002/0178570 to Sogard et al., which is hereby incorporated by reference in its entirety.

The cover 104 can also be coupled to the connection points so as to form the valve leaflets, as discussed herein. In one embodiment, the cover 104 can be in the form of a sheet or a sleeve of material, as discussed herein, which can be connected to the frame 102. Alternatively, the cover 104 can initially be in the form of a liquid that can be used to cast and/or form the cover over the frame 102. Other forms, including intermediate forms, of the cover 104 are also possible.

The cover 104 can be coupled to the frame 102, including the connection points 158 and 160, in a variety of ways so as to provide the various embodiments of the valve of the present invention. For example, a variety of fasteners can be used to couple the cover 104 to the frame 102 so as to form the valve 100. Suitable fasteners can include, but are not limited to, biocompatible staples, glues, sutures or combinations thereof. In an additional embodiment, the cover 104 can be coupled to the frame 102 through the use of heat sealing, solvent bonding, adhesive bonding, or welding cover 104 to either a portion of the cover 104 (i.e., itself) and/or the frame 102.

The cover 104, including the valve leaflets 162 and 164, may also be treated and/or coated with a number of surface or material treatments. For example, the cover 104 can be treated with one or more biologically active compounds and/or materials that may promote and/or inhibit endothelization and/or smooth muscle cell growth of the cover 104, including the valve leaflets 162 and 164. Similarly, the cover 104 may be seeded and covered with cultured tissue cells (e.g., endothelial cells) derived from a either a donor or the host patient which are attached to the valve leaflets 162 and 164. The cultured tissue cells may be initially positioned to extend either partially or fully over the valve leaflets 162 and 164.

Cover 104, in addition to forming valve leaflets 162 and 164, can also be capable of inhibiting thrombus formation. Additionally, cover 104 may either prevent or facilitate tissue ingrowth therethrough, as the particular application for the valve 100 may dictate. For example, cover 104 on the outer surface 152 may be formed from a porous material to facilitate tissue ingrowth therethrough, while cover 104 on the inner surface 154 may be formed from a material or a treated material which inhibits tissue ingrowth.

FIG. 7 illustrates one embodiment of a system 784. System 784 includes valve 700, as described herein, reversibly joined to catheter 786. The catheter 786 includes an elongate body 788 having a proximal end 790 and a distal end 792, where valve 700 can be located between the proximal end 790 and distal end 792. The catheter 786 can further include a lumen 794 longitudinally extending to the distal end 792. In one embodiment, lumen 794 extends between proximal end 790 and distal end 792 of catheter 786. The catheter 786 can further include a guidewire lumen 796 that extends within the elongate body 788, where the guidewire lumen 796 can receive a guidewire for positioning the catheter 786 and the valve 700 within a body lumen (e.g., a vein of a patient).

The system 784 can further include a deployment shaft 798 positioned within lumen 794, and a sheath 701 positioned adjacent the distal end 792. In one embodiment, the valve 700 can be positioned at least partially within the sheath 601 and adjacent the deployment shaft 798. The deployment shaft 798 can be moved within the lumen 794 to deploy valve 700. For example, deployment shaft 798 can be used to push valve 700 from sheath 701 in deploying valve 700.

FIG. 8 illustrates an additional embodiment of the system 884. The catheter 886 includes elongate body 888, lumen 894, a retraction system 803 and a retractable sheath 809. The retractable sheath 809 can be positioned over at least a portion of the elongate body 888, where the retractable sheath 809 can move longitudinally along the elongate body 888. The valve 800 can be positioned at least partially within the retractable sheath 809, where the retractable sheath 809 moves along the elongate body 888 to deploy the valve 800. In one embodiment, retraction system 803 includes one or more wires 895 coupled to the retractable sheath 809, where the wires are positioned at least partially within and extend through lumen 894 in the elongate body 888. Wires of the retraction system 803 can then be used to retract the retractable sheath 809 in deploying valve 800.

Figure 9:
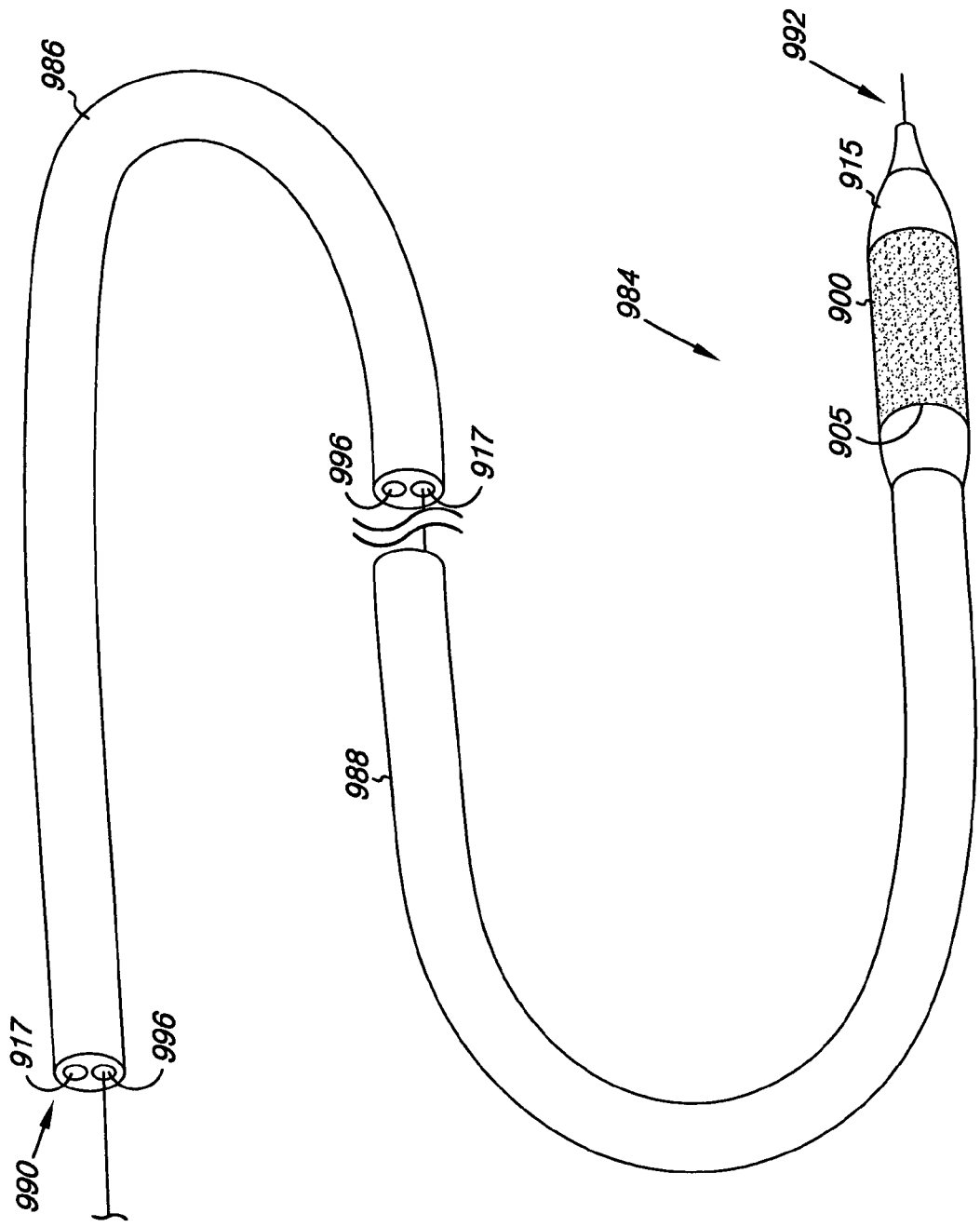
FIG. 9 illustrates an embodiment of a system that includes a valve.

FIG. 9 illustrates an additional embodiment of the system 984. The catheter 986 includes elongate body 988, an inflatable balloon 915 positioned adjacent the distal end 992, and a lumen 917 longitudinally extending in the elongate body 988 of the catheter 986 from the inflatable balloon 915 to the proximal end 990. In the present example, the inflatable balloon 915 can be at least partially positioned within the lumen 905 of the valve 900. The inflatable balloon 915 can be inflated through the lumen 917 to deploy the valve 900.

The embodiments of the present invention further include methods for forming the valve of the present invention, as discussed herein. For example, the valve can be formed from the frame and the cover over at least the outer surface of the frame, where the cover includes surfaces defining the reversibly sealable opening for unidirectional flow of a liquid through the lumen. In an additional example, the valve can be reversibly joined to the catheter, which can include a process of altering the shape of the valve from a first shape, for example an expanded state, to the compressed state, as described herein.

For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present invention may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location. In one embodiment, radiopaque markers on the catheter and/or the valve, as described herein, can be used to help locate and position the valve. For example, embodiments for positioning radiopaque markers on the catheter and/or the valve can be found in co-pending U.S. patent application Ser. No. 11/150, 331, filed on Jun. 10, 2005 and entitled "Venous Valve Frame, System, and Method", which is incorporated herein by reference in its entirety.

The valve can be deployed from the catheter at the predetermined location in a number of ways, as described herein. In one embodiment, valve of the present invention can be deployed and placed in a number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As discussed herein, the valve can be deployed from the catheter in a number of ways. For example, the catheter can include the retractable sheath in which valve can be at least partially housed, as discussed herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as discussed herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the frame 102 and/or the cover 104 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A venous valve, comprising:
   a frame having corner portions that provide a spring force to counter radial compression of the frame and with intermediate portions therebetween, the intermediate portions having a cross-sectional geometry including at least a first planar surface of a predetermined width, where each intermediate portion is twisted about three fourths of a revolution into at least a partial helical configuration and does not intersect with any other intermediate portions, and the corner portions form a first vertex and a second vertex relative a first end of the frame, a third vertex and a fourth vertex at the first end of the frame relative the first and second vertex, where the first vertex and the second vertex are positioned opposite each other along a common axis; and
   a cover on the frame, wherein the cover includes surfaces defining a reversibly sealable opening for unidirectional flow of a liquid through the valve.

2. The venous valve of claim 1, wherein the cross-sectional geometry of intermediate portions of the frame includes a second planar surface parallel with the first planar surface.

3. The venous valve of claim 2, wherein the first planar surface has an essentially symmetrical relation to an outer diameter of the frame.

4. The venous valve of claim 1, wherein the cover extends to at least the first vertex and the second vertex to form a first valve leaflet and a second valve leaflet between the first vertex and the second vertex.

5. The venous valve of claim 4, wherein the first valve leaflet and the second valve leaflet form the reversibly sealable opening extending between the first vertex and the second vertex.

6. The venous valve of claim 1, wherein the at least partial helical configuration imparts a radially expansion force when the frame is radially compressed.

7. The venous valve of claim 1, wherein the cover on the frame includes the cover over an outer surface of the frame.

8. A method, comprising:
   positioning at least part of a catheter including a venous valve at a predetermined location, wherein the venous valve includes:
   a frame having corner portions that provide a spring force to counter radial compression of the frame with intermediate portions therebetween, the intermediate portions having a cross-sectional geometry including at least a first planar surface of a predetermined width, where each intermediate portion is twisted about three quarters of a revolution into at least a partial helical configuration and does not intersect with any other intermediate portions, and the corner portions form a first vertex and a second vertex relative a first end of the frame, a third vertex and a fourth vertex at the first end of the frame relative the first and second vertex, where the first vertex and the second vertex are positioned opposite each other along a common axis;

a cover on the frame, wherein the cover includes surfaces defining a reversibly scalable opening for unidirectional flow of a liquid through the valve; and deploying the venous valve from the catheter at the predetermined location.

9. The method of claim 8, wherein the cover on the frame extends to at least the first vertex and the second vertex to form a first valve leaflet and a second valve leaflet between the first vertex and the second vertex, wherein the first valve leaflet and the second valve leaflet form the reversibly sealable opening extending between the first vertex and the second vertex.

10. The method of claim 8, wherein positioning at least part of the catheter at the predetermined location includes positioning at least part of the catheter within a vein of a leg.

11. The method of claim 8, wherein the catheter includes a retractable sheath, the venous valve at least partially housed within the retractable sheath, and deploying the venous valve from the catheter at the predetermined location includes retracting the retractable sheath of the catheter.

12. The method of claim 8, wherein the catheter includes a deployment shaft and a sheath, the venous valve at least partially housed within the sheath adjacent the deployment shaft, and deploying the venous valve from the catheter at the predetermined location includes moving the deployment shaft to deploy the venous valve from the sheath of the catheter.

13. The method of claim 8, wherein the cross-sectional geometry of intermediate portions of the frame includes a second planar surface parallel with the first planar surface; and the cover extending to at least the first vertex and the second vertex to form a first valve leaflet and a second valve leaflet between the first vertex and the second vertex, wherein the first valve leaflet and the second valve leaflet includes a surface defining a reversibly sealable opening for unidirectional flow of a liquid through the lumen.

14. The method of claim 8, wherein the catheter includes an inflatable balloon, the inflatable balloon at least partially positioned within the lumen of the venous valve; and deploying the venous valve includes inflating the balloon to deploy the vascular valve.

* * * * *